US005733889A

United States Patent [19]
Brown

[11] Patent Number: 5,733,889
[45] Date of Patent: Mar. 31, 1998

[54] TREATMENT FOR CARDIAC ARRHYTHMIAS

[75] Inventor: Arthur M. Brown, Brecksville, Ohio

[73] Assignee: The MetroHealth System, Cleveland, Ohio

[21] Appl. No.: 739,382

[22] Filed: Oct. 29, 1996

[51] Int. Cl.$^6$ ................................................ A61K 31/70
[52] U.S. Cl. ................................................................ 514/46
[58] Field of Search ................................................ 514/46

[56] References Cited

U.S. PATENT DOCUMENTS 4,560,795 12/1985 Bey et al.
5,416,076 5/1995 Casara et al. ............................. 514/46

OTHER PUBLICATIONS

"Regulation by Spermine of Native Inward Rectifier K+ Channels in RBL–1 Cells" by Bianchi, et al., J. Biol. Chem. 271(11), pp. 6114–6121, Mar. 1996.
"Effects of the S–adenosylmethione decarboxylase inhibitor ..." by Byers, et al., Biochem J. 303(1), pp. 89–96, 1994.
"Polyamine–mediated regulation of S–adenosylmethione decarobxylase ..." by Stjernborg, et al., Eur. J. Biochem. 214, pp. 671–676 (1993).
"Effects of chronic 5'{[(Z)–4–amino–2–butenyl]methylamino}–..." by Byers, et al., Biochem. J., 290(1), pp. 115–121, 1993.
"Inhibition of S–adenosyl–L–methionine (Adomet) Decarboxylase ..." by Yakubu, et al., J. Parasitol, 79(4) pp. 525–532, 1993.

*Primary Examiner*—Raymond Henley, III
*Attorney, Agent, or Firm*—Calfee, Halter & Griswold LLP

[57] ABSTRACT

The present invention provides a novel treatment for cardiac arrhythmias, by administering S-adenosyl methionine decarboxylase inhibitors, preferably 5'-({(Z)-4-amino-2-butenyl}methylamino)-5'-deoxyadenosine. It has been discovered that 5'-({(Z)-4-amino-2-butenyl}methylamino)-5'-deoxyadenosine, increases the P—R interval, increases outward current through inward rectifier K$^+$ channels and increases the hyperpolarization, of cardiac cells, thereby reducing cardiac excitability. Specifically, the method involves providing an S-adenosyl methionine decarboxylase inhibitor; combining the S-adenosyl methionine decarboxylase inhibitor with a pharmaceutically acceptable carrier to provide a pharmaceutical composition; administering an effective amount of the pharmaceutical composition to a patient suffering from a cardiac arrhythmia, wether such arrhythmias are induced by disease or cardiotoxicity. As a result of the treatment with S-adenosyl methionine decarboxylase inhibitor, spermine and spermidine levels are lowered in cardiac cells, the P—R interval is prolonged, cardiac excitability is reduced and the incidence of ventricular fibrillation, particularly sustained ventricular fibrillation is diminished. The method of the present invention is useful to terminate, prevent or reduce the incidence of cardiac arrhythmias, including, for example, ventricular tachycardia, atrial fibrillation ventricular fibrillation, particularly sustained ventricular fibrillation, and premature ventricular contractions.

10 Claims, 3 Drawing Sheets

TREATMENT FOR CARDIAC ARRHYTHMIAS

BACKGROUND OF THE INVENTION

Cardiac arrhythmias, a common cause of death, occur when electrically-coupled excitable cells of the heart are at different membrane potentials, in particular when some cells are depolarized relative to others. Current methods typically involve treating such arrhythmias in the acute stage, with calcium channel blockers, sodium channel blockers, potassium channel blockers and beta adreno-receptor blockers. Attempts have been made to treat chronic heart arrhythmias "prophlactically with such calcium channel blockers and beta adreno-receptor blockers; such attempts have mixed success. Often such drugs tend to be nonspecific and block other cardiac membrane channels, in particular sodium channels and potassium channels which leads to a disruption in conduction. Indeed, the method of conventional therapy for the largest subgroup of arrhythmias, re-entrant arrhythmias, has been to block repolarizing potassium currents which are responsible for terminating the cardiac action potential, thereby prolonging the action potential. Unfortunately few drugs are successful, and those that are, also suffer from disadvantages, such as torsade de pointes.

It is desirable to have a method for reducing cardiac arrhythmias, that is specific and does not interfere with other ion channels.

SUMMARY OF THE INVENTION

The present invention provides a novel treatment for cardiac arrhythmias, by administering S-adenosyl methionine decarboxylase inhibitors, preferably 5'-({(Z)-4-amino-2-butenyl}methylamino)-5'-deoxyadenosine. It has been discovered that 5'-({(Z)-4-amino-2-butenyl}methylamino)-5'-deoxyadenosine, increases the P—R interval, increases outward current through inward rectifier $K^+$ channels and increases the hyperpolarization, of cardiac cells, thereby reducing cardiac excitability. Specifically, the method involves providing an S-adenosyl methionine decarboxylase inhibitor; combining the S-adenosyl methionine decarboxylase inhibitor with a pharmaceutically acceptable carrier to provide a pharmaceutical composition; administering an effective amount of the pharmaceutical composition to a patient suffering from a cardiac arrhythmia, whether such arrhythmias are induced by disease or cardiotoxicity. As a result of the treatment with S-adenosyl methionine decarboxylase inhibitor, spermine and spermidine levels are lowered in cardiac cells, the P—R interval is prolonged, cardiac excitability is reduced and the incidence of ventricular fibrillation, particularly sustained ventricular fibrillation is diminished. The method of the present invention is useful to terminate, prevent or reduce the incidence of cardiac arrhythmias, including, for example, ventricular tachycardia, atrial fibrillation ventricular fibrillation, particularly sustained ventricular fibrillation, and premature ventricular contractions.

DETAILED DESCRIPTION OF THE INVENTION

Figure 1:
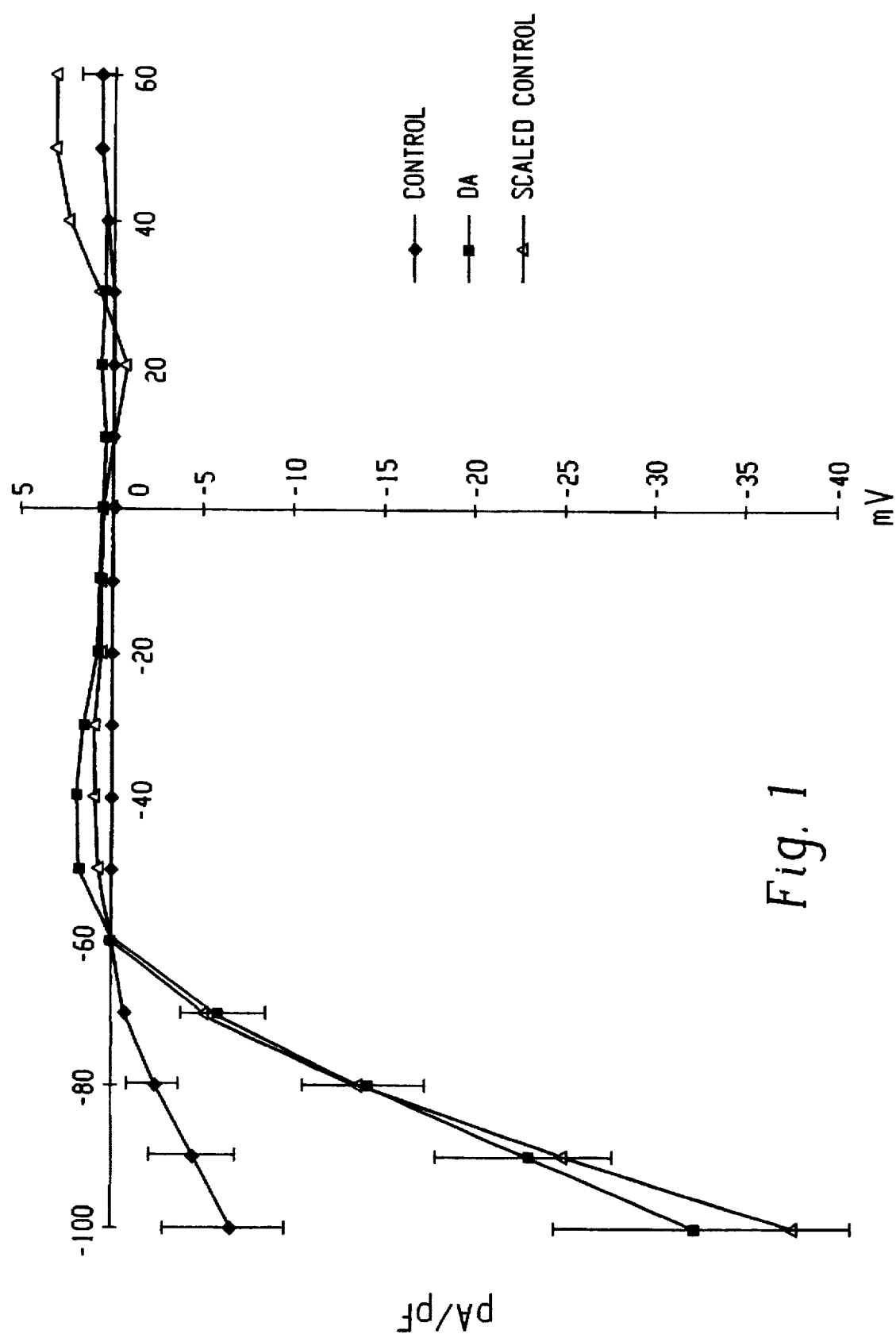
FIG. 1 is a graph showing the current-voltage relation for $Ba^{2+}$ sensitive current from neonatal rat cardiomyocytes treated with 5'-({(Z)-4-amino-2-butenyl}methylamino)-5'-deoxyadenosine, also referred to herein as "DA", in example 1. Current values are plotted as means +/− standard error of the mean. Control data, designated by diamonds ♦, are the means from two cardiomyocytes, and the DA data, designated by squares ■, are the means from three cardiomyocytes. A scaled control designated by open triangle ∆, is also shown.

The present invention provides a novel treatment for cardiac arrhythmias, by administering S-adenosyl methionine decarboxylase inhibitors, preferably 5'-({(Z)-4-amino-2-butenyl}methylamino)-5'-deoxyadenosine. It has been discovered that 5'-({(Z)-4-amino-2-butenyl}methylamino)-5'-deoxyadenosine, increases the P—R interval, increases outward current through inward rectifier $K^+$ channels and increases the hyperpolarization, of cardiac cells, thereby reducing cardiac excitability. Specifically, the method involves providing an S-adenosyl methionine decarboxylase inhibitor; combining the S-adenosyl methionine decarboxylase inhibitor with a pharmaceutically acceptable carrier to provide a pharmaceutical composition; administering an effective amount of the pharmaceutical composition to a patient suffering from a cardiac arrhythmia, wether such arrhythmias are induced by disease or cardiotoxicity. As a result of the treatment with S-adenosyl methionine decarboxylase inhibitor, spermine and spermidine levels are lowered in cardiac cells, the P—R interval is prolonged, cardiac excitability is reduced and the incidence of ventricular fibrillation, particularly sustained ventricular fibrillation is diminished. The method of the present invention is useful to terminate, prevent or reduce the incidence of cardiac arrhythmias, including, for example, ventricular tachycardia, atrial fibrillation ventricular fibrillation, particularly sustained ventricular fibrillation, and premature ventricular contractions.

The intracellular cationic polyamines, spermine and spermidine block inward rectifier $K^+$ channels. These channels set the resting potential of heart cells and are involved in terminal repolarization of the cardiac action potential. It has been discovered that spermine levels may be lowered in cardiac cells, by employing S-adenosyl methionine decarboxylase inhibitors, which inhibit the synthesis of spermine. It has also been discovered that the outward current, that is, the outward flow of $K^+$, is increased through inward rectifier $K^+$ channels of cardiac cells by employing S-adenosyl methionine decarboxylase inhibitors. It has also been discovered that the hyperpolarization phase of conduction in cardiac cells is prolonged upon treatment with S-adenosyl methionine decarboxylase inhibitors.

Particularly in diseased cardiac tissue, in which the resting potential is not as polarized relative to normal resting potential in normal cardiac tissue, the S-adenosyl methionine decarboxylase inhibitors increase the polarization from typically about −50 or −60 to about −80 mV. As a result, the cardiac cells are less excitable, that is, the cells are less likely to fire an action potential, particularly in response to an irregular beats generated during fibrillation and tachycardia. As a result, the associated arrhythmias are reduced.

A particular advantage of the present invention is that the S-adenosyl methionine decarboxylase inhibitors are specific to cellular polyamines which in turn are specific for inward recktifier potassium channels. Since spermine and spermidine do not play a role in the function of other channels in the cardiac cellular membrane, such as calcium channels, sodium channels, chloride channels, voltage gated potassium channels 1.4, 1.5, 2.1, 2.2, 4.2, 4.3, the HERG potassium channel and minimum potassium channels, such channels are not effected by the S-adenosyl methionine decarboxylase inhibitors.

The methods of the present invention employ S-adenosyl methionine decarboxylase inhibitors having the following structure:

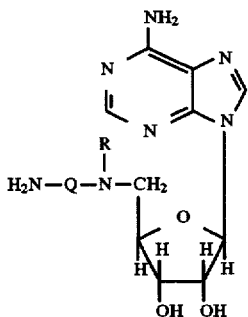

wherein

Q is:

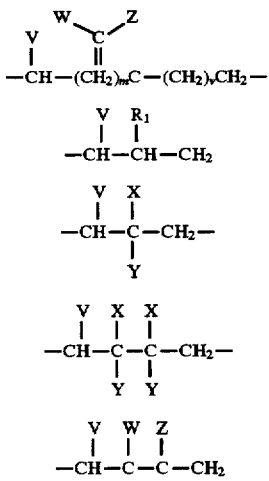

R is H or an alkyl group having from one to seven carbon atoms;

$R_1$ is:

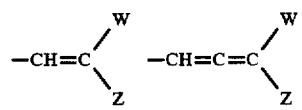

W is H, F, Cl, BR;
V is H, COOH;
X is H or F;
Y is H or F;
Z is H, F, Cl, BR;
and the pharmaceutically acceptable salts thereof.
Preferably the inhibitors have the following structures:

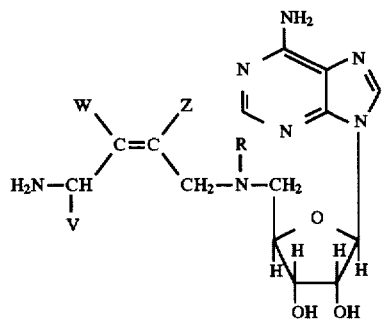

wherein:
R is H or an alkyl group having from one to seven carbon atoms;
W is H, F, Cl or Br;
V is H or COOH;
Z is H, F, Cl or Br;
and the pharmaceutically acceptable salts thereof. Where V is H, R is a methyl group, x is H and z is H, the compound is 5'-({(Z)-4-amino-2-butenyl}methylamino)-5'-deoxyadenosine.

Effective amounts, that is, suitable dosage levels of the S-adenosyl methionine decarboxylase inhibitors preferably range from about 0.2 to 1000 mg/kg body weight of the patient, more preferably from about 1 to 500 mg/kg, preferably from about 10 to 250 mg/kg. The S-adenosyl methionine decarboxylase inhibitor is preferably mixed with pharmaceutically acceptable carrier. Preferred pharmaceutically acceptable carriers for injection include, for example, sterile saline and distilled water. The S-adenosyl methionine decarboxylase inhibitor, preferably 5'-({(Z)-4-amino-2-butenyl}methylamino)-5'-deoxyadenosine, may be injected as a solution or suspension or compounded with a pharmaceutically acceptable carrier such as gelatin, lactose, sucrose, cornstarch or and formed into a tablet, capsule, syrup or the like. Routes of administration include, for example, oral, sublingual, intramuscular, intraperitoneal, intravenous and the like. Other forms of administration are discussed in U.S. Pat. No. 5,416,076, which has been incorporated herein by reference.

As a prophylactic, the S-adenosyl methionine decarboxylase inhibitor is administered preferably orally in regular periodic dosages preferably from one to 4 times a day, or administered continually in the form of an implant below the skin. As a treatment for accute episodes of cardiac arryhthmias, the S-adenosyl methionine decarboxylase inhibitor is administered as a chemical defibrilator preferably by intravenous injection, to terminate the fibrillation episode and reduce the onset of sustained ventricular fibrillation.

Materials and Techniques

"Defined media" contains DMEM/F12 supplemented with 10% fetal bovine serum and gentamicin; the media and supplements were obtained from Gibco BRL, Grand Island, N.Y.

"Chemically-defined media" contains DMEM/12 supplemented with 1.0 g/L insulin, 0.55 mg/L transferrin, 0.67 mg/L selenium and 0.2 g/L ethanolamine. This solution is sold as ITS-X (100×) from Gibco, and is diluted to 1× in the media. All media and supplements were obtained from Gibco BRL, Grand Island, N.Y.

The inhibitors are made as described in U.S. Pat. No. 5,416,076, issued May 16, 1996, assigned to Merrel Dow Pharmaceuticals Inc. which are fully incorporated herein by reference. 5'-({(Z)-4-amino-2-butenyl}methylamino)-5'-deoxyadenosine, was obtained from Merrel Dow Pharmaceuticals Inc., and may be synthesized as described in U.S. Pat. No. 5,416,076, or in "5'-({(Z)-4-Amino-2-butenyl}methylamino)-5-deoxyadenosine: A Potent Enzyme-Activated Irreversible Inhibitor of S-Adenosyl-L-methionine Decarboxylase from *Escherichia coli* Journal of the American Chemical Society, (1989) Volume III, Number 25, pages 9111–9113 which is fully incorporated herein by reference.

Preparation of Cardiomyocytes

Sprague-Daewley 1 day old neonatal rat hearts were collected into ice-cold $Ca^{2+}$ and $Mg^{2+}$ free Hank's balanced salt solution, ventricles separated from atria and vessels; and ventricles were minced with scissors. The resulting small chunks of ventricular tissue were added to 10 ml of $Ca^{2+}$ and $Mg^{2+}$ free Hank's balanced salt solution containing 500 µg/ml of trypsin Type II-S from Sigma, St. Louis, Mo., and incubated for about 12 to 16 hours in a petri dish in the refrigerator. The ventricular tissue chunks were washed with ice-cold $Ca^{2+}$ and $Mg^{2+}$ free Hank's balanced salt solution to remove the trypsin, warmed to room temperature and resuspended in DMEM/F12 media supplemented with 10% bovine calf serum, 50 µg/ml gentamicin and 100 U/ml of Collagenase Type I from Worthington, Freehold, N.J. and incubated for 30 to 45 minutes at 37° C. in an orbital shaking water bath at 40 to 60 cycles/second. The cells were dispersed with gentle trituration and washed with $Ca^{2+}$ and $Mg^{2+}$ free Hank's balanced salt solution to remove collagenese. The cells were plated on 3 mm square glass coverslips at a density of 50,000 cells/cm$^2$ in DMEM/F12 media supplemented with 10% bovine calf serum and 50 µg/ml gentamicin. On the following day myocyte cultures were changed to defined media, as outlined in the examples.

Determination of Intracellular Polyamine Levels

Cellular polyamines were determined as described in J. J. Moore, et al., Journal of Biological Chemistry, (1988) volume 263, pages 12765–12769. Cardiomyocytes were washed twice with ice cold phosphate-buffered saline, scraped from wells, and frozen at −80° C. Thawed samples were later sonicated, and proteins were precipitated with perchloric acid. 1,7-diaminoheptane was added as an internal standard, then samples were neutralized with $K_2CO_3$, and the polyamines were derivatized with 5-dimethylaminonapthalene-1-sylfonyl chloride.

The derivatized polyamines were partially purified with SepPak $C_{18}$ cartridges. Samples were further fractionated by HPLC, employing a Partisil-10 ODS column and two different solvents; the first was a mixture of 92.5% acetonitrile and 7.5% methanol hereinafter referred to as "Solvent A" and the second was 10 mM monopotassium phosphate at pH 4.4, hereinafter referred to as "Solvent B". First, the column was equilibrated with a mixture of 35% Solvent A and 65% Solvent B. One minute after sample injection, a linear gradient to 60% Solvent A was carried out. The gradient was then increased to 90% Solvent A over 5 minutes and held there for an additional 20 minutes. The column effluent was monitored with a fluorescence detector using an excitation filter of 305–395 nm and an emission filter of 435–650 nm.

Putrescine, spermidine, and spermine standards were carried through the entire procedure to establish column retention times and calibration curves for each polyamine. Concentrations were expressed as nmol of polyamine/µg of DNA and given as means +/− S.E. DNA concentrations were measured according to the method of Burton K., Journal of Biological Chemistry, (1956) volume 62, pages 315–319.

Electrophysiological Recordings

The square glass coverslips containing myocytes, were placed in a plastic chamber on the stage of a Zeiss IM35 inverted microscope and superfused with a $Ca^{2+}$ free Tyrode's solution of the following composition (in mM): NaCl 137, KCl 5.4, $MgCl_2$ 5, HEPES 5, glucose 10, pH 7.4 with NaOH. For solution changes, an array of 100 µm-bore capillary tubes was positioned next to the cells by manually repositioning the capillaries to superfuse the cell with different solutions flowing from each capillary, solutions flowing over the cell were changed in 5 to 10 seconds. Cells were superfused with the $Ca^{2+}$ free Tyrode's solution from the capillary array during recording of current voltage relations. The solution was switched to $Ca^{2+}$ free Tyrode's with the addition of 100 µM $Ba^{2+}$ to block inward rectifier currents. The internal solution of the pipette contained: 112 mM K-aspartate, 4 mM $MgCl_2$, 4 mM EGTA, 4 mM $Na_2ATP$, HEPES 8, 8 mM glucose, at pH 7.2 adjusted with KOH.

Patch pipettes were fabricated from Corning 7052 glass and fire polished just before use. An Axopatch 200A from Axon instruments, Foster City, Calif., was used for voltage clamp of the myocytes with the whole cell recording configuration of the patch clamp technique. PClamp software from Axon Instruments, Foster City, Calif. and hardware was used for data acquisition and analysis. Data was analog filtered at 0.2 of the sampling frequency with an 8-pole Bessel filter before analog to digital conversion. All work was performed at room temperature.

Current-voltage relations for the cardiac inward rectifier were calculated as the difference of current-voltage relations obtained in $Ca^{2+}$ free Tyrode's solutions without and with the addition of 100 µM $Ba^{2+}$ to block the inward rectifier currents. Currents are expressed as densities to normalize cell surface area. The myocyte capacitance was calculated from capacity current transients produced by 10 mV voltage steps.

The following Examples are intended to be illustrative the and not limiting.

EXAMPLE 1

Cultures of confluent electrically coupled cardiac myocytes, prepared as described above, were grown 24 hours and then the media was replaced with the defined media. The defined media contained either 50 µM 5'-({(Z)-4-amino-2-butenyl}methylamino)-5'-deoxyadenosine, or 500 µM DFMO. The control cultures were handled in the same manner but without the addition of either drug. The cells were incubated for 48 hours, then the inward rectifier currents were measured and recorded. The results are shown in FIG. 1.

In the control cultures, the confluent myocytes beat; in cultures treated with the 5'-({(Z)-4-amino-2-butenyl}methylamino)-5'-deoxyadenosine, the myocytes cease to beat indicating that cardiac excitability is reduced.

The current through the inward rectifier $K^+$ channels (called $I_{K1}$ in cardiomyocytes) was increased, relative to the controls, as shown in FIG. 1. Thus 5'-({(Z)-4-amino-2-butenyl}methylamino)-5'-deoxyadenosine reduces cardiac excitability.

EXAMPLE 1A

Figure 2A:
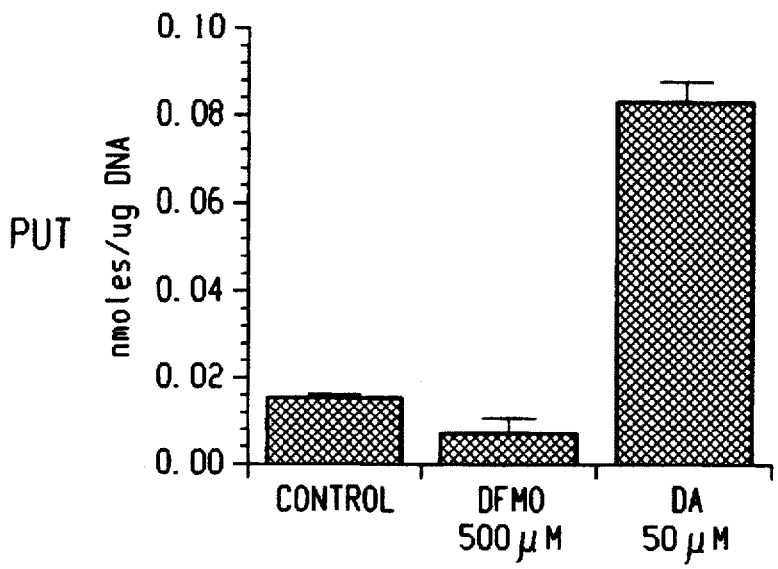
FIG. 2a is a graph showing the intracellular putrescine (PUT), concentration of cultured rat cardiomyocytes of Example 2. Controls are shown in the left column, (n=9); cells exposed to 500 µM difluoromethyl ornithine, hereinafter also referred to as "DFMO", are shown in the middle column, (n=6) and cells exposed to 50 µM 5'-({(Z)-4-amino-2-butenyl}methylamino)-5,'-deoxyadenosine, are shown in the right column (n=8). Concentrations are given as means +/− S.E.
Figure 2B:
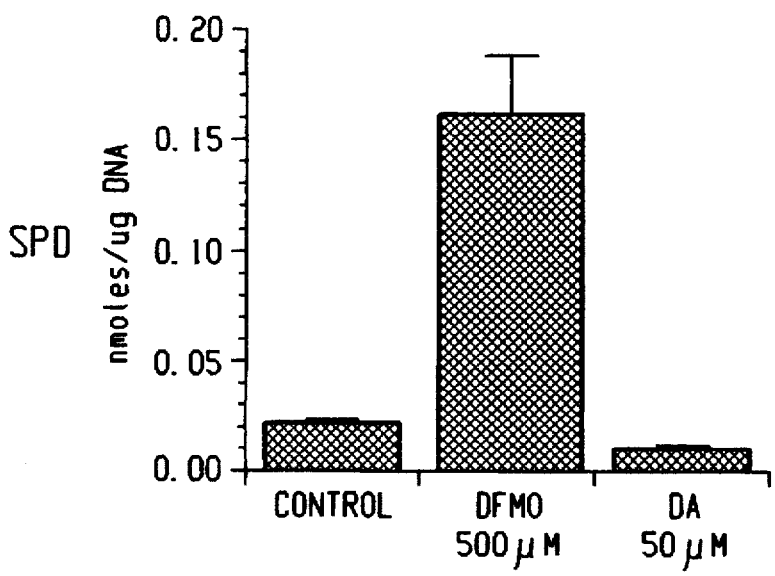
FIG. 2b is a graph showing the intracellular spermidine (SPD), concentration of cultured rat cardiomyocytes (left column, n=9) and cells exposed for two days to either 500 µM DFMO (middle column, n=6) or 50 µM 5'-({(Z)-4-amino-2-butenyl}methylamino)-5'-deoxyadenosine (right column, n=8). Concentrations are given as means +/− S.E.
Figure 2C:
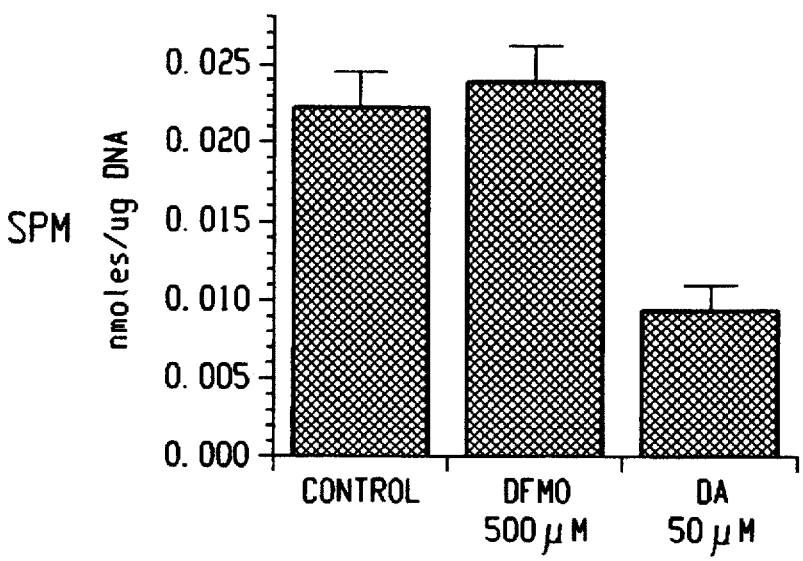
FIG. 2c is a graph showing the intracellular spermine (SPM) concentration of cultured rat cardiomyocytes (left column, n=9) and cells exposed for two days to either 500 µM DFMO (middle column, n=6) or 50 µM 5'-({(Z)-4-amino-2-butenyl}methylamino)-5'-deoxyadenosine (right column, n=8). Concentrations are given as means +/− S.E.
Figure 3:
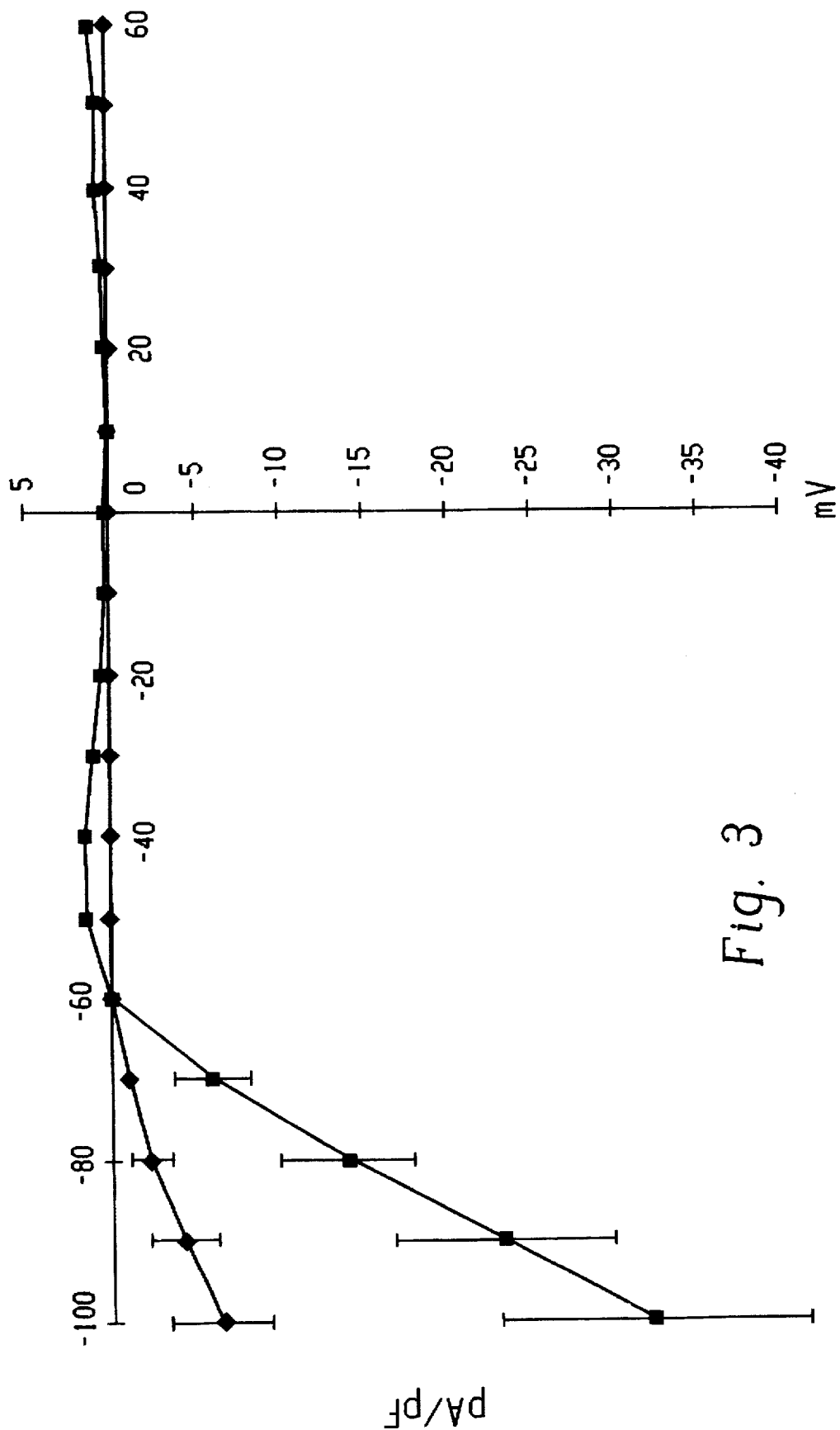

Cardiomyocyte cultures were prepared as in Example 1, except that after 48 hours, they were harvested and the intracellular polyamine levels were determined. The results are presented in FIGS. 2A–C.

As shown in FIG. 2, the 5'-({(Z)-4-amino-2-butenyl}methylamino)-5'-deoxyadenosine, lowered spermine and spermidine levels in the cardiomyocytes as compared both the control cells and the in DMFO treated cells.

EXAMPLE 2

5'-({(Z)-4-amino-2-butenyl}methylamino)-5'-deoxyadenosine was dissolved in saline, and the solution was injected at a dosage of 100 mg/kg intraperitoneally into nine day old Wistar rats. Rats provide a model of ventricular fibrillation, see M. Curtis and D. Hearse "Reperfusion-induced Arrhythmias are Critically Dependent upon Occluded Zone Size: Relevance to the Mechanism of Arrhythmogenesis", Journal of Molecular Cellular Cardiology,(1989) volume 21, pages 625 to 637. Ten control rats were handled in the same manner except that they received a placebo solution of saline that did not contain the 5'-({(Z)-4-amino-2-butenyl}methylamino)-5'-deoxyadenosine. Two to six hours later, the coronary flow rate, heart rate and electrocardiogram were measured. The 5'-({(Z)-4-amino-2-butenyl}methylamino)-5'-deoxyadenosine did not affect the coronary flow rate, heart rate or QT interval. The coronary arteries of the rats were then occluded for 30 minutes to induce myocardial ischemia, and the incidence of ventricular fibrillation and sustained ventricular fibrillation was determined during the ischemia. The data was analyzed and is presented in Tables I and II.

TABLE I

Effect of 5'-({(Z)-4-amino-2-butenyl}methylamino)-5'-deoxyadenosine on P-R Interval

| P-R Interval (ms) -5 Control | DA |
|---|---|
| 44 | 46 |
| 36 | 40 |
| 33 | 44 |
| 36 | 52 |
| 39 | 38 |
| 38 | 36 |
| 35 | 40 |
| 35 | 31 |
| 33 | 44 |
| 36 | |

TABLE II

| | Incidence of Ventricular Fibrillation | | Incidence of Sustained Ventricular Fibrillation in: | | | |
|---|---|---|---|---|---|---|
| | | | Rats with Ventricular Fibrillation: | | All Rats: | |
| | No. | % | No. | % | No. | % |
| Control Rats | 9/10 | 90% | 6/9 | 67% | 6/10 | 60% |
| Treated Rats | 6/9 | 67% | 2/6 | 33% | 2/9 | 22.2% |

As shown in Table I, prior to the induced ischemia, the electrocardiograms revealed that treatment with the 5'-({(Z)-4-amino-2-butenyl}methylamino)-5'-deoxyadenosine lengthened the P—R interval, that is the time between the beginning of the P wave (as seen on and EKG) which corresponds to the beginning of the depolarization of the atria, and the beginning of the QRS complex, which corresponds to the beginning of the ventricular depolarization. The P—R interval was prolonged from 36.5+/− 1.0 ms in the controls, to 41.3 +/− 2 in the rats treated with 5'-({(Z)-4-amino-2-butenyl}methylamino)-5'-deoxyadenosine ($p<0.05$). This lengthening of the P—R interval demonstrates that the 5'-({(Z)-4-amino-2-butenyl}methylamino)-5'-deoxyadenosine decreases the conductivity of the heart. The 5'-({(Z)-4-amino-2-butenyl}methylamino)-5'-deoxyadenosine, by increasing the P—R interval, is useful to slow ventricular tachycardia, particularly the ventricular tachycardia that follows atrial tachycardia, atrial flutter, and atrial fibrillation, so that the ventricles respond to only a portion of the atrial "beats". The S-adenosyl methionine decarboxylase inhibitor are also useful to counteract conditions which shorten the P—R interval such as anemia, and various thyroid conditions. The S-adenosyl methionine decarboxylase inhibitors are also useful as a treatment for atrial fibrillation brought on by disease or by cardiac by-pass surgery.

As can be seen in Table II, six out of nine rats treated with the 5'-({(Z)-4-amino-2-butenyl}methylamino)-5'-deoxyadenosine suffered ventricular fibrillation as compared to nine out of ten rats in the control group. Significantly, 5'-({(Z)-4-amino-2-butenyl}methylamino)-5'-deoxyadenosine decreased the incidence of sustained ventricular fibrillation. Sustained ventricular fibrillation, which is an episode of ventricular fibrillation which lasts for 2 or more minutes, poses the risk to the patient. Sixty-seven percent of controls displayed sustained ventricular fibrillation during the ischemic period compared to only 33% of the rats treated with 5'-({(Z)-4-amino-2-butenyl}methylamino)-5'-deoxyadenosine.

As can be seen in FIG. 2, the 5'-({(Z)-4-amino-2-butenyl}methylamino)-5'-deoxyadenosine increased the current through the inward rectifier $K^+$ channels, that is the $K^+$ flow outward was increased. In rats treated with the S-adenosyl methionine decarboxylase inhibitor no torsade de pointes were observed on the EKG.

The method of reducing cardiac excitability is not only useful in treatment of various cardiac conditions in human and veterinary patients, but also in research, experimentation, and the study of conduction processes in the mammalian heart.

While embodiments of the invention have been shown and described, various adaptations and modifications can be made without departing from the scope of invention as defined in the appended claims.

What is claimed is:

1. A method for reducing cardiac excitability in a patient comprising the following steps:

providing an S-adenosyl methionine decarboxylase inhibitor;

combining the S-adenosyl methionine decarboxylase inhibitor with a pharmaceutically acceptable carrier to provide a pharmaceutical composition;

administering an effective amount of the pharmaceutical composition to the patient having cardiac arrhythmias, wherein the occurrence of the cardiac arrhythmias is reduced.

2. The method of claim 1 wherein the S-adenosyl methionine decarboxylase inhibitor has the following structure:

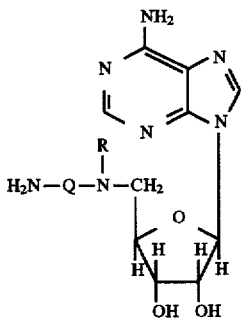

wherein

Q is:

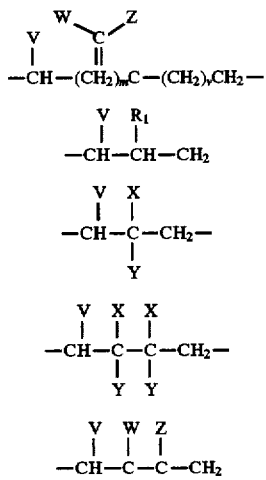

R is H or an alkyl group having from one to seven carbon atoms;

$R_1$ is:

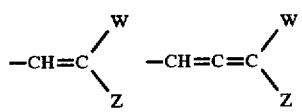

W is H, F, Cl or Br;
V is H or COOH;
X is H or F;
Y is H or F; and
Z is H, F, Cl or Br.

3. The method of claim 1, wherein the S-adenosyl methionine decarboxylase inhibitor has the following structure:

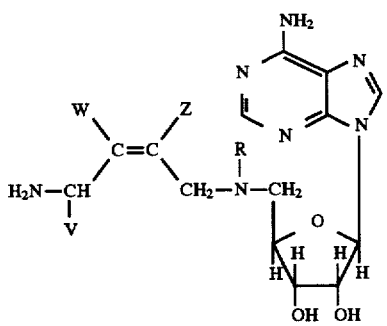

wherein:
   R is H or an alkyl group having from one to seven carbon atoms;
   W is H, F, Cl or Br;
   V is H or COOH; and
   Z is H, F, Cl or Br.

4. The method of claim 1, wherein the S-adenosyl methionine decarboxylase inhibitor is 5'-({(Z)-4-amino-2-butenyl}methylamino)-5'-deoxyadenosine.

5. The method of claim 1, wherein the pharmaceutical composition is administered during an episode of cardiac arrhythmia.

6. The method of claim 1, wherein the pharmaceutical composition is administered prophlactically.

7. The method of claim 1, wherein the cardiac arrhythmia is ventricular fibrillation.

8. The method of claim 1, wherein the cardiac arrhythmia is an atrial arrhythmia, and the time between the beginning of the depolarization of the atria and the beginning of the ventricular depolarization, is increased.

9. The method of claim 7, where the ventricular fibrillation is sustained fibrillation.

10. The method of claim 1, wherein the arrhythmia is tachycardia.

* * * * *